United States Patent [19]

Brittain et al.

[11] 4,443,465

[45] Apr. 17, 1984

[54] ALDOSE REDUCTASE INHIBITORY PYRROLE DERIVATIVES

[75] Inventors: David R. Brittain, Macclesfield; Robin Wood, Hazel Grove, both of England

[73] Assignee: Imperial Chemical Industries PLC, London, England

[21] Appl. No.: 377,133

[22] Filed: May 11, 1982

[30] Foreign Application Priority Data

May 12, 1981 [GB] United Kingdom ............... 8114402

[51] Int. Cl.³ ............... A61K 31/415; C07D 493/20; C07D 495/20
[52] U.S. Cl. ............................ 424/273 R; 424/262; 546/10; 546/15; 546/84; 548/101; 548/309; 548/431
[58] Field of Search ............... 548/309, 101; 542/401; 424/273 R

[56] References Cited

U.S. PATENT DOCUMENTS

| | | | |
|---|---|---|---|
| 4,117,230 | 9/1978 | Sarges | 548/309 |
| 4,127,665 | 11/1978 | Sarges et al. | 548/309 X |
| 4,181,728 | 1/1980 | Sarges et al. | 548/309 X |
| 4,248,882 | 2/1981 | Sarges et al. | 548/309 X |

*Primary Examiner*—Richard A. Schwartz
*Attorney, Agent, or Firm*—Cushman, Darby & Cushman

[57] ABSTRACT

The invention provides an aldose reductase inhibitory pyrrole derivative of the formula:

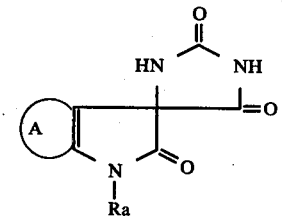

in which Ra is an optionally substituted benzyl or cinnamyl radical, and ring A is the benzene ring of an optionally substituted benzo[b]thiophene, benzo[b]furan, quinoline or N-alkylquinolone, together with pharmaceutically acceptable salts and non-toxic biodegradable precursors thereof.

The compounds of formula I are useful in the treatment of prophylaxis of the side-effects of diabetes or galactosemia.

9 Claims, No Drawings

ALDOSE REDUCTASE INHIBITORY PYRROLE DERIVATIVES

This invention relates to novel pyrrole derivatives and, more particularly, to novel 1-substituted-spiro[4-pyrroline-3,4'-imidazolidine]-2,2',5'-triones which possess the property of inhibiting the enzyme aldose reductase in vivo and are of use in the treatment or prophylaxis of certain complications of protracted diabetes or galactosemia.

The enzyme aldose reductase is responsible for the catalytic conversion of aldoses, for example glucose and galactose, to the corresponding alditols, for example sorbitol and galactitol respectively. Alditols penetrate cell membranes poorly and, once formed, tend to be removed only by further metabolism. As a consequence, alditols tend to accumulate within cells where they are formed, causing a rise in internal osmotic pressure which may in turn be sufficient to destroy or impair the function of the cells themselves. In addition, raised alditol levels may result in abnormal levels of their metabolites which may themselves impair or damage cellular function. However, the enzyme aldose reductase has a relatively low substrate affinity, that is, it is only effective in the presence of relatively large concentrations of aldose. Such large concentrations of aldose are present in the clinical conditions of diabetes (excessive glucose) and galactosemia (excessive galactose). As a consequence, inhibitors of the enzyme aldose reductase are useful in the reduction or prevention of the development of those complications of protracted diabetes or galactosemia which may be due in part to the accumulation of sorbitol or galactitol respectively. Such complications are, for example, macular oedema, cataract, retinopathy, nephropathy or impaired neural conduction.

It is known that certain spiro-linked hydantoins (spiro-linked imidazolidine-2,5-diones) derived from various bicyclic ketones are inhibitors of the enzyme aldose reductase, for example the compounds of the general formula:

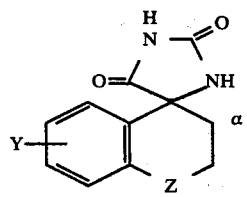

wherein Z is oxygen, sulphur, sulphinyl, sulphonyl, methylene or a direct bond, and Y stands for various optional substituents described by Sarges in U.S. Pat. Ser. No. 4,117,230. We have now discovered that certain spiro-linked hydantoins of the formula I below derived from tricyclic 1-substituted-4-pyrrolidine-2,3-diones possess useful aldose reductase inhibitory properties and this is the basis for our invention.

This discovery is surprising in view of the various chemical differences involved, for example in view of the presence of an amidic carbonyl radical in the α-position relative to the spiro-carbon atom, which position is always occupied by a methylene radical in the aldose reductase inhibitory spiro-hydantoins of the prior art.

According to the invention there is provided a 1-substituted-spiro[4-pyrroline-3,4'-imidazolidine]2,2',5'-trione of the formula:

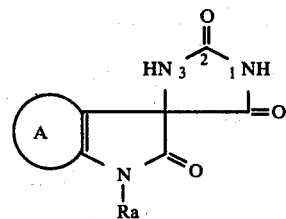

wherein Ra is a benzyl radical optionally bearing up to three substituents independently selected from halogeno, trifluoromethyl, (1–4C)alkyl, (1–4C)alkoxy, nitro, (1–4C)alkylthio and cyano radicals; or a halogenocinnamyl radical; and ring A stands for the benzene ring of a benzo[b]thiophene, benzo[b]furan, quinoline or N-(1–4C)-alkyl-2- or -4-quinolone which may bear one or two substituents independently selected from (1–4C)alkyl, (1–4C)alkoxy and phenyl substituents located on the benzene or heterocyclic ring; or a pharmaceutically acceptable base-addition salt thereof; or a non-toxic, biodegradable precursor thereof.

In this specification the symbols Ra and Rb, et cetera, denote generic radicals and have no other significance.

The compounds of formula I possess at least one asymmetric carbon atom, namely the spiro-linked carbon atom. They therefore exist, and may be isolated, in racemic and optionally-active forms. This invention relates to the racemic form of a compound of formula I or to any optionally-active form which possesses aldose reductase inhibitory properties, it being well known in the art how to prepare optionally active forms by resolution of the racemic form, or by synthesis from optically-active starting materials, and how to determine the aldose reductase inhibitory properties by the standard tests described hereinbelow.

Particular values for substituents which may be present on Ra or on ring A are, for example:

for a halogeno, a fluoro, chloro, bromo or iodo radical;

for a (1–4C)alkyl, a methyl or ethyl radical;

for a (1–4C)alkoxy, a methoxy or ethoxy radical; and for a (1–4C)alkylthio, a methylthio or ethylthio radical.

Specific values for ring A when it is an N-(1–4C)alkyl-2- or -4-quinolone are, for example, N-methyl-2-quinoline, N-ethyl-2-quinolone or N-methyl-4-quinolone.

Particular groups of compounds of the invention which are of special interest are as follows:

(a) those compounds of the formula:

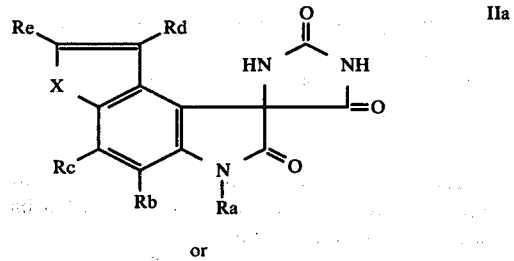

or

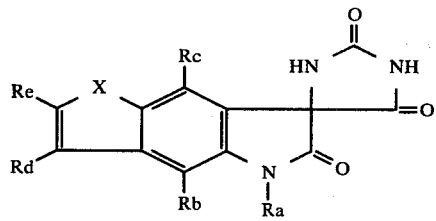

IIb wherein X is oxygen or sulphur, Rb, Rc and Rd are independently selected from hydrogen, (1–4C)alkyl and (1–4C)alkoxy radicals, and Re is hydrogen or a (1–4C)-alkyl or phenyl radical;

(b) those compounds of the formula:

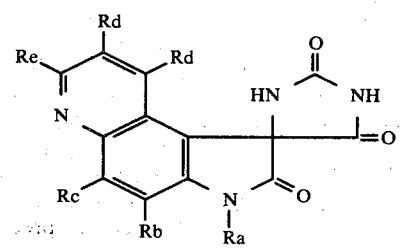

IIIa or

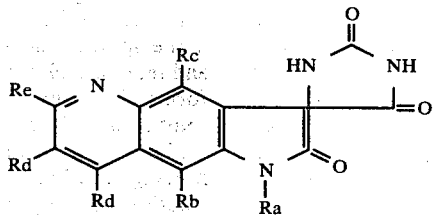

IIIb wherein Rb, Rc, Rd and Re have the meanings defined above;

(c) those compounds of the formula:

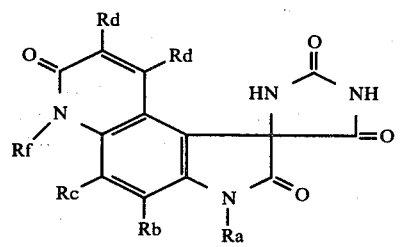

IVa or

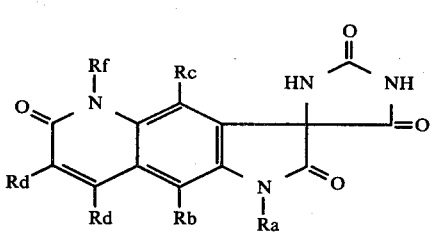

IVb wherein Rf is a (1–4C)alkyl radical, for example a methyl or ethyl radical, and Rb, Rc and Rd have the meanings defined above; and (d) those compounds of the formula:

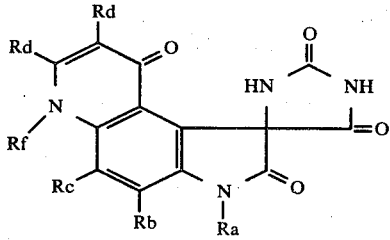

Va or

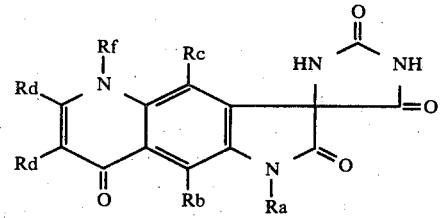

Vb wherein Rf, Rb, Rc and Rd have the meanings defined above; and in each group Ra has the meanings defined earlier, and together with the pharmaceutically acceptable base-addition salts and non-toxic, biodegradable precursors thereof.

The term non-toxic, biodegradable precursor includes derivatives of the compounds of formula I defined above in which one or both of the imino hydrogen atoms in the hydantoin ring are replaced by biodegradable protecting radicals known in the art, which radicals are not inherently toxic and which are capable of removal in vivo (for example by enzymic hydrolysis) to liberate the compound of formula I in sufficient quantity to inhibit the enzyme aldose reductase and without giving rise to pharmacologically unacceptable by-products. Examples of suitable radicals for inclusion in biodegradable precursors of compounds of formula I include alkoxycarbonyl, aralkoxycarbonyl, alkoxyoxalyl and 1-(alkylcarbonyloxy)alkyl radicals, such as ethoxycarbonyl, t-butyloxycarbonyl, benzyloxycarbonyl, ethoxyoxalyl, methoxyoxalyl and pivaloyloxymethyl radicals. The biodegradable precursors are not, in general, themselves inhibitors of the enzyme aldose reductase, but are active in vivo by virtue of removal of the biodegradable protecting radical. It will be apparent therefore that by suitable choice of biodegradable protecting radicals (for example based on their generally known rates of enzymic degradation) it is possible to produce biodegradable precursors of compounds of formula I whose bioabsorption and distribution properties differ from those of the compounds of formula I.

A preferred value for Ra is when it is a benzyl radical bearing one or two halogeno radicals for example when it is a 4-halogeno-, 2,4-dihalogeno-, 3,4-dihalogeno- or 3,5-dihalogeno-benzyl radical, such as a 4-bromo-, 4-bromo-2-fluoro, 2-fluoro-4-iodo-,3,4-dichloro-, 4-bromo-3-chloro- or 3,5-dichloro-benzyl radical; or when it is a halogenocinnamyl radical, is, for example a 4-chloro-, 4-bromo- or 3,4-dichlorocinnamyl radical.

Particular base-addition salts of compounds of formula I are those with bases affording a pharmaceutically acceptable cation, for example, alkali metal or alkaline earth metal salts such as sodium, potassium, calcium or magnesium salts, aluminium or ammonium salts or salts with organic bases such as triethanolamine.

The compounds of formula I may be obtained by any process known in the art for the manufacture of structurally analogous compounds. Such processes are provided as a further feature of the invention and are illustrated by the following procedures wherein Ra and ring A have the meanings defined hereinbefore:

(a) Reacting a 4-pyrroline-2,3-dione of the formula:

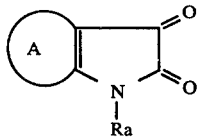
VI with an alkali metal cyanide and ammonium carbonate or carbamate.

A suitable alkali metal cyanide is, for example, sodium or potassium cyanide.

It will be understood this process is an example of the Bücherer-Bergs synthesis of imidazolidine-2,4-diones (hydantoins) which is well known in the art (see E. Ware in Chemical Reviews, 1950, 46, 422–425), and that such a reaction may therefore proceed through a hydroxynitrile of the formula:

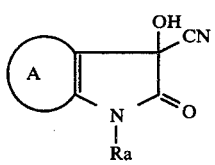
VII and/or an amino-nitrile of the formula:

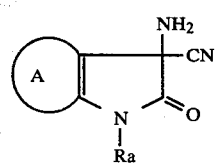
VIII

Accordingly, the invention includes carrying out process (a) by separate or in situ manufacture of an intermediate of formula VII (for example by reaction of a compound of formula VI with hydrogen cyanide) followed by reaction of the intermediate with ammonium carbonate or carbamate. Similarly, the invention includes carrying out process (a) by separate or in situ manufacture of an intermediate of formula VIII (for example by reacting a compound of formula VI with ammonia and hydrogen cyanide) followed by reaction of the intermediate with carbon dioxide, which may conveniently be provided as ammonium carbonate or carbamate.

The process may be conveniently performed in a solvent or diluent, for example in a (1–4C)alkanol such as methanol or ethanol, or in ethylene glycol or diethylene glycol, preferably containing water, and at a temperature in the range, for example 20°–100° C.

The ammonium carbonate or carbamate may if necessary be formed in situ in conventional manner.

The starting materials of formula VI may be obtained by conventional procedures of heterocyclic chemistry.

Thus, for example, they may be obtained by reacting the corresponding compound of the formula

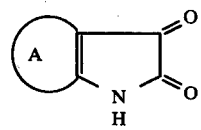
IX with the appropriate aralkyl or aralkenyl chloride, bromide or iodide, in the presence of a base, such as sodium or potassium hydroxide or sodium hydride, in dimethyl sulphoxide at a temperature in the range 20° to 40° C.

The compounds of formula IX are isatin derivatives and may be obtained by known syntheses of isatins, for example by reacting the appropriate amino-benzheterocycle with chloral hydrate followed by oxime formation and cyclisation, for example in the presence of an acid such as polyphosphoric acid.

Examples of suitable compounds of formula IX are shown below:

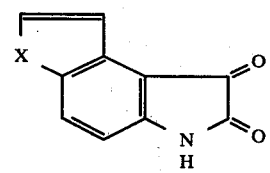
Xa

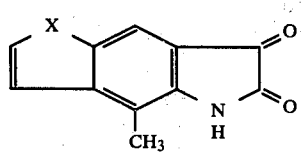
Xb

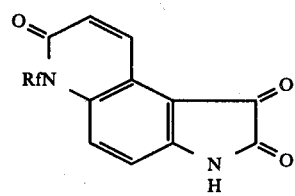
Xc

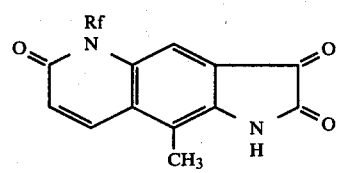
Xd

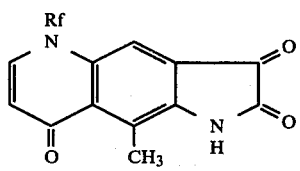
Xe

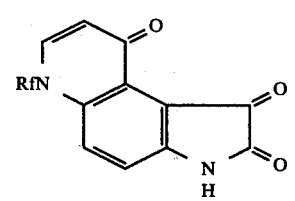
Xf wherein X is oxygen or sulphur and Rf is methyl or ethyl. These compounds may be obtained from the corresponding amino-benzheterocycle, as illustrated for Xa (X=sulphur) in the accompanying Example 1.

(b) Reacting a compound of the formula:

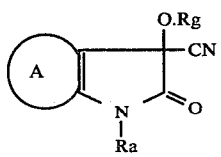

wherein Rg is an acyl or tri-[(1–4C)alkyl]silyl radical with ammonium carbonate or carbamate.

A particular value for Rg when it is an acyl radical is, for example, a (1–6C)alkanoyl radical such as an acetyl or propionyl radical, a phenylsulphonyl, toluene, p-sulphonyl or benzoyl radical.

It will be recognised that process (b) is a modification of process (a) hereinbefore and consequently similar reaction conditions may be used. Similarly the ammonium carbonate or carbamate may be formed in situ if desired.

The starting materials of formula XI may be made by conventional procedures. Thus, they may be obtained by reacting a hydroxynitrile of formula VII (itself obtained as described in process (a) by reaction of an isatin derivative with cyanide) with an appropriate acyl or tri-[(1–4C)alkyl]silyl halide, for example acetyl, propionyl, phenylsulphonyl, toluene-p-sulphonyl, benzoyl or trimethylsilyl chloride, in conventional manner.

Alternatively, those compounds of formula XI wherein Rg is a tri-[(1–4C)alkyl]silyl radical may be conveniently obtained by reaction of an appropriate isatin derivative with a tri-[(1–4C)alkyl]silyl cyanide, for example trimethylsilyl cyanide, at a temperature in the range, for example, 15°–40° C. and in a non-aqueous solvent, for example 1,2-dimethoxyethane.

The non-toxic, biodegradable precursors of the compounds of formula I may be obtained by known acylation or alkylation procedures already used for the introduction of the necessary biodegradable protecting radicals. Examples of suitable acylating or alkylating reagents for incorporating a range of such protecting radicals are, for example, alkoxycarbonyl, aralkoxycarbonyl, alkoxyoxalyl and 1-(alkoxycarbonyloxy)alkyl halides, such as ethoxycarbonyl, t-butyloxycarbonyl, benzyloxycarbonyl, ethoxyoxalyl, methoxyoxalyl and pivaloyloxymethyl chloride.

The reaction may be performed under conventional N-acylation/alkylation conditions, for example in the presence of a base such as potassium carbonate or using the lithium, sodium or potassium salt of the compound of formula I and in a suitable solvent or diluent, for example 1,2-dimethoxyethane, di-n-butyl ether or diethyl ether, at a temperature in the range, for example 10°–80° C. Depending on the amount of alkylating or acylating agent and the base employed, it is possible to obtain either mono- or di-substituted precursors. In general it is preferred to have the imidazolidine ring bear only one biodegradable protecting radical located at position 1. When a pharmaceutically acceptable base-addition salt is required, a compound of formula I is reacted with a suitable base affording a pharmaceutically acceptable cation, using a conventional procedure.

Further, when an optically-active form of a compound of formula I is required, a racemic form of said compound may be reacted with an optically-active form of a suitable organic base, for example brucine, coniine, 2-pipecoline or an N,N,N-trialkyl-(1-phenylethyl)ammonium hydroxide such as N,N,N-trimethyl-(1-phenylethyl)ammonium hydroxide, followed by conventional separation of the diastereoisomeric mixture of salts or complexes thus obtained, for example by fractional crystallisation from a suitable solvent, for example a (1–4C)alkanol, whereafter the optically-active form of the said compound may be liberated by treatment with acid using a conventional procedure for example using an aqueous mineral acid such as dilute hydrochloric acid.

The property of inhibiting the enzyme aldose reductase may be demonstrated in the following standard laboratory test. Thus, rats are made diabetic (as evidenced by severe glucosuria being present) by dosing with streptozotocin. The animals are then dosed daily with the test compound for 5 days. The animals are then killed and the eye lenses and sciatic nerves are removed. After a standard work-up procedure, the residual sorbitol levels in each tissue are determined by gas liquid chromatography, after conversion to the poly-trimethylsilyl derivatives. Inhibition of aldose reductase in vivo is then assessed by comparing the residual sorbitol levels in tissues from the dosed diabetic group of rats with those of an undosed group of diabetic rats and an undosed, normal group of rats.

Alternatively, a modified test may be used in which the streptozotocin induced diabetic rats are dosed daily with test compound for two days. After 2–4 hours from the final dose, the animals are killed and the sciatic nerves are removed and assessed for residual sorbitol levels as described above.

Preferred compounds in either of these tests reduce residual sorbitol levels to levels which are similar to those of normal, undosed rats. However, in general the compounds of formula I produce significant inhibition of the enzyme aldose reductase at an oral dose of 100 mg./kg. or much less with no overt toxicity at the active dose.

The property of inhibiting the enzyme aldose reductase may also be demonstrated in vitro. Thus, purified aldose reductase is isolated in known manner from bovine lenses. The percentage inhibition of this enzyme's ability in vitro to reduce aldoses to polyhydric alcohols, and particularly to reduce glucose to sorbitol, caused by a test compound is then determined using standard spectrophotometric methods. In this test the compounds of formula I in general show significant inhibition of the enzyme aldose reductase at a concentration of about $10^{-6}$ M or much less.

When a compound of the invention is used to produce an effect on the enzyme aldose reductase in warm-blooded animals, it may be administered primarily orally at a daily dose of for example 0.5 to 25 mg./kg, and in man a total daily dose in the range 10 to 750 mg. per man will be administered, given in divided doses if necessary.

The compounds of the invention may be administered in the form of pharmaceutical compositions and according to a further feature of the invention there is provided a pharmaceutical composition which comprises a derivative of formula I, together with a pharmaceutically acceptable diluent or carrier.

Especially preferred pharmaceutical compositions are those which are in a form suitable for oral administration, for example tablets, capsules, suspensions or solutions, which may be obtained by conventional methods and, if desired, may incorporate conventional diluents, carriers or other excipients. Other preferred compositions are those which are in a form suitable for parenteral administration, for example sterile injectable aqueous or non-aqueous solutions or suspensions, and for rectal administration, for example suppositories.

Topical formulations may be administered to the eye of an animal, for example man or dogs, requiring treatment for diabetic cataracts or retinopathy in a conventional manner for example using a drop or eyewash topical formulation.

The invention also provides a method for inhibiting aldose reductase in an animal requiring such treatment which method comprises administering to said animal an aldose reductase inhibitory amount of a compound of formula I as defined or a pharmaceutically acceptable salt thereof.

The compositions of the invention may also contain one or more other agents which may or are known to have a useful effect in the treatment of diabetes or galactosemia, for example a hypoglycaemic agent such as tolbutamide, chlorpropamide, or glybenclamide.

The invention will now be illustrated in the following non-limiting Examples in which, unless otherwise stated:

(i) all evaporations were carried out by rotary evaporation in vacuo;

(ii) all operations were carried out at room temperature, that is in the range 18°–26° C.;

(iii) petroleum ether (b.p. 60°–80° C.) is referred to as "petrol 60–80"; and (iv) yields are given for illustration only and are not necessarily the maximum attainable:

EXAMPLE 1

Trimethylsilyl cyanide (0.6 g.) was added to a solution of 6-[3,4-dichlorobenzyl]thieno[3,2-e]-indoline-7,8-dione (1.45 g.) in dimethoxyethane (25 ml.) containing zinc iodide (0.1 g.). The mixture was stirred for 1 hour and then a solution of ammonium carbonate (5.0 g.) in water (40 ml.) was added. The mixture obtained was heated at 95°–100° C. under reflux for 24 hours and cooled to ambient temperature. Potassium cyanide (1.0 g.), ammonium carbonate (5.0 g.) and ethanol (20 ml.) were added to the cooled solution and the mixture was heated under reflux for a further 24 hours at 95°–100° C.

The mixture was then cooled to 10° C. and adjusted to pH 5 with 2 M hydrochloric acid. The solid which precipitated was collected by filtration and purified by chromatography on silica gel using an increasing concentration of ethyl acetate in toluene as eluant. There was thus obtained 6'-(3,4-dichlorobenzyl)-spiro(imidazolidine-4,8'-thieno[3,2-e]indoline)-2,5,7'-trione (0.1 g.), m.p. 231°–233° C. [after crystallisation from toluene/petrol 60-80 (1:1 v/v].

The starting material was obtained as follows: Sodium sulphate (8.1 g.) and chloral hydrate (1.1 g.) in water (25 ml.) were added to a suspension of 5-aminobenzthiophen (1.0 g.) in 1 N hydrochloric acid (6.7 ml.) A solution of hydroxylamine hydrochloride (1.5 g.) in water (4 ml.) was then added to this stirred mixture. The temperature of the mixture was then raised to 100° C., held at this temperature for 45 minutes and then cooled to 20° C. The mixture was then diluted with water (100 ml.). The solid which precipitated was collected by filtration washed with water and dried at 45° C. in vacuo to give, 5-(β-isonitrosoacetamido)benzthiophene (0.9 g.), m.p. 180°–182° C.

A mixture of 5-(β-isonitrosoacetamido)benzthiophene (1.5 g.) and polyphosphoric acid (15 g.) was warmed to 55° C. and stirred at this temperature for 15 minutes and then at 85° C. for a further 15 minutes. The mixture was then cooled to ambient temperature and diluted with a slurry of ice and water (100 ml.). The solid which separated was collected by filtration, washed with water, dried in vacuo ($P_4O_{10}$) and extracted with ethyl acetate in a Soxhlet extractor. The extracts were evaporated and the residue was recrystallised from ethyl acetate and petroleum ether (1:1 v/v) to give thieno[3,2-e]indoline-7,8 dione (1.1 g.), m.p. 268°–269° C.

Ethanolic potassium hydroxide solution (7.4 ml; 1 M solution) was added to a solution of thieno[3,2-e]indoline-7,8-dione (1.35 g.) in dimethyl sulphoxide (10 ml.). The mixture was stirred for 10 minutes and then 3,4-dichlorobenzyl chloride (1.5 g.) was added in a single portion. The subsequent mixture was stirred for 12 hours and then diluted with water (150 ml.) The solid which formed was collected by filtration, washed with water, then with petrol 60-80 and dried in vacuo at 45° C. ($P_4O_{10}$). There was thus obtained 6-(3,4-dichlorobenzyl)-thieno[3,2-e]indoline-7,8-dione (1.5 g.), m.p. 200°–201° C.

EXAMPLE 2 (All parts by weight)

A mixture of 6'-(3,4-dichlorobenzyl)-spiro(imidazolidine-4,8'-thieno[3,2-e]indoline)-2,5,7'-trione (50 parts), lactose (27 parts) and maize starch (20 parts) was stirred thoroughly and a paste formed from maize starch (2 parts) and water (40 parts) was added and thoroughly mixed in. The resultant mass was passed through a 16 mesh screen, then dried at 60° C. and passed through a 20 mesh screen. Magnesium stearate (1 part) was added to the granules obtained, and the whole compressed by conventional means into tablets, containing 10, 20, 50 and 100 mg. of active ingredient and suitable for oral administration for therapeutic purposes.

What is claimed is:

1. A 1-substituted-spiro[4-pyrroline-3,4'-imidazolidine]-2,2',5'-trione of the formula:

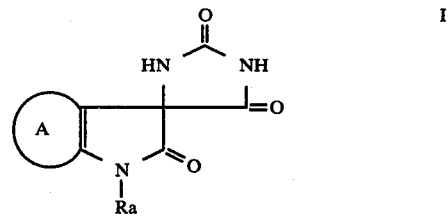

wherein Ra is a benzyl radical optionally bearing up to three substituents independently selected from halogeno, trifluoromethyl, (1–4 C)alkyl, (1–4 C)alkoxy, nitro, (1–4 C)alkylthio and cyano radicals; or a halogenocinnamyl radical; and ring A stands for the benzene ring of a benzo[b]thiophene or benzo[b]furan which may bear one or two substituents independently selected from (1–4 C)alkyl, (1–4 C)alkoxy and phenyl substituents located on the benzene or heterocyclic ring; or a pharmaceutically acceptable base-addition salt thereof; or a non-toxic, biodegradable precursor thereof.

2. A compound of formula I wherein Ra is a benzyl radical optionally bearing up to three substituents independently selected from fluoro, chloro, bromo, iodo, trifluoromethyl, methyl, ethyl, methoxy, ethoxy, nitro, methylthio, ethylthio and cyano radicals; or a cinnamyl radical bearing one or two halogeno radicals independently selected from fluoro, chloro, bromo and iodo radicals; and ring A stands for the benzene ring of a benzo[b]thiophene or benzo[b]furan which may bear one or two substituents independently selected from methyl, ethyl, methoxy, ethoxy and phenyl radicals.

3. A compound as claimed in claim 1 wherein Ra is a 4-halogeno-, 2,4-dihalogeno-, 3,4-dihalogeno- or 3,5-dihalogeno-benzyl, or a dihalogenocinnamyl radical;

4. A compound as claimed in claim 3 wherein Ra is a 4-bromo-, 4-bromo-2-fluoro-, 2-fluoro-4-iodo-, 3,4-dichloro-, 4-bromo-3-chloro- or 3,5-dichlorobenzyl, or a 4-chloro-, 4-bromo- or 3,4-dichloro-cinnamyl radical.

5. 6'-(3,4-Dichlorobenzyl)-spiro[imidazoline-4,8'-thieno[3,2-e]indoline]-2,5,7'-trione; or a pharmaceutically acceptable base-addition salt thereof; or a non-toxic biodegradable precursor thereof.

6. A salt of a compound of formula I as claimed in claim 1 which is an alkali metal, alkaline earth metal, aluminium, ammonium or triethanolamine salt.

7. A pharmaceutical composition suitable for inhibiting the enzyme aldose reductase which comprises as active ingredient an effective amount of a 1-substituted-spiro[4-pyrroline-3,4'-imidazolidine]-2-2', 5-trione of the formula I, or a pharmaceutically acceptable base-addition salt thereof, or a non-toxic biodegradable precursor thereof, as claimed in claim 1; together with a pharmaceutically acceptable diluent or carrier.

8. A composition as claimed in claim 7 which is in a form suitable for oral, parenteral, rectal or topical administration.

9. A method of inhibiting the enzyme aldose reductase in a warm-blooded animal requiring such treatment which comprises administering to said animal an aldose reductase inhibitory amount of a 1-substituted-sprio[4-pyrroline-3,4'-imidazolidine]-2,2',5'-trione of the formula I, or a pharmaceutically acceptable base-addition salt thereof, or a non-toxic biodegradable precursor thereof as claimed in claim 1.

* * * * *